United States Patent [19]

Curtis

[11] Patent Number: 4,797,000
[45] Date of Patent: Jan. 10, 1989

[54] COMPARATIVE COLORIMETER

[75] Inventor: Richard H. Curtis, Gorham, Me.

[73] Assignee: Artel, South Windham, Me.

[21] Appl. No.: 815,522

[22] Filed: Jan. 2, 1986

[51] Int. Cl.[4] .............................................. C01N 21/53
[52] U.S. Cl. ..................................... 356/436; 356/435; 356/409
[58] Field of Search ............... 356/432, 433, 434, 435, 356/436, 441, 409, 414, 225, 442

[56] References Cited

U.S. PATENT DOCUMENTS

| 2,501,599 | 3/1950 | Eltenton et al. | 356/435 |
|---|---|---|---|
| 2,617,940 | 11/1952 | Giguere | 356/435 |
| 2,873,644 | 2/1959 | Kremen et al. | 356/435 |
| 3,498,719 | 3/1970 | Wing et al. | 356/142 |
| 3,989,383 | 11/1976 | Paulson | 356/414 |
| 4,006,990 | 2/1977 | Munk | 356/434 |
| 4,193,694 | 3/1980 | Smith | 356/414 |
| 4,195,932 | 4/1980 | Popelka | 356/414 |
| 4,310,249 | 1/1982 | Kramer | 356/414 |

FOREIGN PATENT DOCUMENTS

2069692 8/1981 United Kingdom ............... 356/435

Primary Examiner—Richard A. Rosenberger
Attorney, Agent, or Firm—Wolf, Greenfield & Sacks

[57] ABSTRACT

A comparitive colorimeter for use in the field which simultaneously compares the color densities of two liquid samples and designates the degree of difference. The apparatus includes two major subsystems, optical and electronic. The optical subsystem is designed to provide identical light beams through both the sample and standard solutions and to minimize the effect which imperfect sample tubes have on the output. The electronic subsystem includes a log conversion and differential amplifier circuit for generating a difference signal representative of the difference between the optical densities of the sample and standard solutions. The difference signal is evaluated by a comparative circuit consisting of a resistive chain having a plurality of node voltages and hex inverters connected to the node voltages. The hex inverters drive a series of LED indicator lights to designate the relative degree of difference between the optical densities of the sample and standard. A correction circuit is provided for referencing the difference signal to the threshold voltage of the hex inverters and for compensating for initial differences in the optical paths of the sample and standard solutions.

8 Claims, 5 Drawing Sheets

COMPARATIVE COLORIMETER

BACKGROUND OF THE INVENTION

This invention relates to a comparative colorimeter, and more specifically to an instrument which simultaneously compares the color (i.e., optical) densities of two liquid samples and designates the degree of difference. A colorimeter is useful for conducting:

(a) medical diagnostic tests based on enzyme immuno assays (EIA), e.g., the test for Leutenizing Hormone as an indication of ovulation in humans;

(b) medical diagnostic tests based on Enzyme Multiplied Immuno assay Technique (EMIT), e.g., tests for drugs of abuse such as barbituates;

(c) veterinary diagnostic tests based on either (a) or (b), e.g., progesterone level in dairy cows;

(d) environmental tests based on either (a) or (b), e.g., residual Chlorodane levels after extermination around residences; and (e) determination of the concentration of certain chemicals based on absorption of a given wavelength of light, e.g., concentration of the herbicide Dynaseb TM.

In the above-identified tests, it is generally not the absolute value of optical density of a solution which is of interest, but rather a comparison of a sample solution with a standard solution. Further, while all of these tests can be satisfactorily performed in the laboratory using a standard off-the-shelf spectrophotometric instrument, such instruments are delicate and expensive and are not adapted for use in the field. For example, a colorimeter is useful in the field to determine whether the residual level of a pesticide applied to a crop has declined sufficiently to allow safe entry of personnel into the field for harvesting operations.

A known colorimeter used in the field performs separate quantitative determinations of the optical densities of a sample solution and a standard solution. The human operator then computes the difference between the quantitative determinations. This device has several disadvantages. First, since the operator is generally interested in only the relative difference between the sample and standard, it is a waste of effort to make a quantitative determination for each of the sample and standard. Further, since the quantitative determinations of the sample and standard are made at different times, there exists a large potential for error if either of the solutions changes in optical density with respect to time or temperature.

It is an object of the present invention to provide a relatively low-cost comparative colorimeter for use in the field for comparing the optical densities of two solutions and indicating the relative degree of difference.

It is another object of this invention to provide a comparative colorimeter for simultaneously evaluating the optical densities of sample and standard solutions prepared at the same time in order to eliminate any error caused by changes in the optical densities of the sample and standard with respect to time.

It is a further object of this invention to provide an optical subsystem for a colorimeter which reduces the error caused by defects in the sample tube such as scratches, irregularities or striations in the tube wall, and lack of concentricity.

It is still another object of this invention to provide an electronic subsystem, including low-cost digital integrated circuits, for quantifying the difference between the optical densities of the sample and standard solutions.

It is a still further object of this invention to provide a correction circuit to compensate for variations in the threshold voltage of the digital IC components with respect to batch, time, temperature, and supply voltage.

It is still another object of this invention to provide a correction circuit to compensate for differences in the optical paths of the sample and standard solutions.

SUMMARY OF THE INVENTION

The apparatus of this invention provides a means for simultaneously comparing the optical densities of two solutions and generating an output indicative of the degree of difference. The apparatus includes two major subsystems, optical and electronic.

The optical subsystem is designed to provide identical light paths through two liquid samples disposed in optically transparent sample tubes and to minimize the effect which imperfect sample tubes have on the measurement. The optical subsystem includes a light source means for transmitting a pair of substantially equal light beams, one to each of a pair of photodetectors. Each of the two liquid samples are simultaneously and identically positioned between the light source means and an associated photodetector. The photodetectors generate a pair of optical density output signals representative of the amounts of light passing through the samples and reaching the photodetectors. The optical system is designed to spread the light over a substantial portion of each sample tube to minimize the effect of defects in the tubes.

In one embodiment of the optical system of this invention, a collimating lens is positioned between the sample tube and light source and spaced slightly closer to the light source than the focal point of the lens so that the lens transmits a slightly divergent beam of light to the tube. The tube is spaced with respect to the lens so that the outer diameter of the divergent beam at the center plane of the tube is substantially equal to the inner diameter of the tube. The sample tube acts as a cylinder lens to focus the beam at a vertical focal line, and the photodetector is spaced slightly ahead of the focal line so that the beam strikes a substantial portion of the photodetector. The photodetector output is substantially independent of defects in the sample tube.

Preferably, the optical system further includes a combination filter/diffuser positioned between the sample tube and photodetector. The filter/diffuser includes a filter for selecting a predetermined wavelength of light and a light diffusing layer for averaging the effect of individual defects in the sample tube so that the photodetector output is less affected by such defects. Preferably, the light diffusing layer is disposed over the surface of the filter adjacent the photodetector. In a further preferred embodiment, a plurality of such combination filter/diffusers are connected in serial arrangement and the photodetector is positioned adjoining a light diffusing layer at one end of the series.

In a second embodiment of the optical system of this invention, a first lens set is positioned between the sample tube and light source. The first lens set includes a first collimating lens disposed adjacent the light source and having a focal point at the light source, and a first converging lens disposed adjacent the sample tube and having a focal point at the center of the sample tube. A second lens set is positioned between the sample tube and photodetector. The second lens set includes a second collimating lens disposed adjacent the sample tube and having a focal point at the center of the tube, and a second converging lens disposed adjacent the photodetector and having a focal point at the photodetector. Because in this second embodiment the light rays pass perpendicularly through the tube and the tube has no focusing effect, refraction is reduced and irregularities in the tube do not affect the focus point. Thus, the accuracy of this second embodiment is less dependent on the spacing between the lenses and tube than that of the first embodiment. A filter may be positioned between the two lenses of the second lens set, and because the light passes through the filter in parallel rays, there is minimal reflection at the filter surface and thus minimal light loss.

The electronic subsystem of this invention provides a high level of accuracy and stability despite the stringent cost limitations imposed by the intended application. In particular, the circuit utilizes low-cost digital components to achieve a quantified output indicative of the degree of difference in optical densities of the two samples. A correction circuit is provided to compensate for variations in the threshold voltage of the digital IC components and to compensate for differences in the optical paths of the two samples.

The electronic subsystem includes a differential circuit means for generating a difference signal representative of the difference between the optical density output signals of the photodetectors. The system further includes a comparative circuit including means for comparing the difference signal to a plurality of predetermined references and a means for indicating the relative value of said difference signal with respect to said predetermined references.

In a preferred embodiment, the current outputs of a pair of photodiodes are logarithmically converted to voltage signals and the resultant voltage signals are differentially amplified to produce a difference signal. The difference signal is sent to a resistive chain including a plurality of nodes, each node having a different predetermined reference voltage. A plurality of digital gate means each having the same threshhold voltage are each connected to one of said nodes. The outputs of the gate means activate a plurality of indicator means to indicate the relative value of the difference signal with respect to the predetermined reference voltages.

In addition, a correction circuit is provided for referencing the difference signal to the threshold voltage of the gate means. The correction circuit includes an additional gate means from the same batch used in the comparative circuit. The output of the correction circuit, which is referenced to the threshold voltage of the gate means, is applied to the comparative circuit so that the difference signal is referenced to the threshold voltage. Further, the correction circuit includes a zeroing mechanism to compensate for differences in the light paths of the two sample solutions.

DETAILED DESCRIPTION OF THE INVENTION

Figure 1:
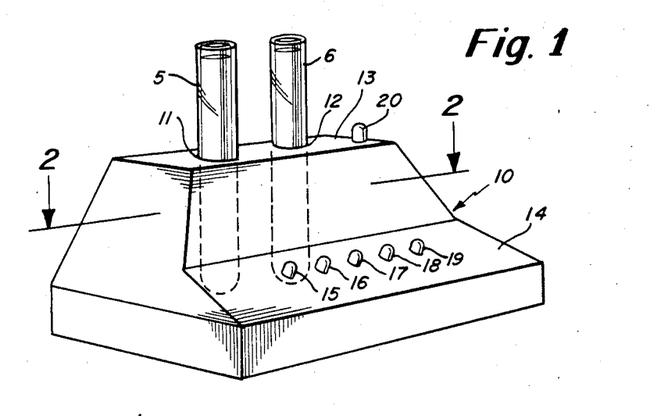
FIG. 1 is a perspective view of the comparative colorimeter of this invention.

FIG. 1 is a perspective view of the comparative colorimeter of the present invention. A housing 10 contains the optical and electronic subsystems of this invention. A pair of sample tube holders 11, 12 consist of tubular bores disposed vertically in the housing and having closed lower ends and open upper ends in the top wall 13 of the housing. The holders snugly engage two cylindrical sample tubes 5, 6 which contain the sample and standard solutions respectively. A row of five indicator lights 15, 16, 17, 18, 19 is provided on the front wall 14 of the housing. An on-off button 20 is provided on top wall 13 of the housing. The housing is made of a nonbreakable plastic such as acrylonitrile-butadiene-styrene polymer. The device shown in FIG. 1 is compact and portable, being 5" (127 mm) wide, 2.5" (64 mm) high, 3" (76 mm) deep, and weighing about 200 grams. Typically, sample tubes 5, 6 are made of polystyrene and have outer dimensions of 12 mm in diameter and 75 mm in length, and an inner diameter of 9 mm.

The comparative colorimeter of this invention consists of two major subsystems, optical and electronic. The important features of the optical subsystem include:

(a) it must provide equal light paths through both of the sample tubes; to the extent that the light paths are not identical, then the ratio of light going through them must be constant despite: the buildup of dirt and contamination; thermal effects; warping or flexing of the printed circuit board or other structural members; mechanical shock and abuse; and aging of various components, e.g., light bulb and filters;

(b) it must provide adequate light intensity at the photodiodes under all operating conditions;

(c) it must minimize the effects of stray or ambient light; and (d) it must minimize the effect of imperfect sample tubes.

In a laboratory spectrophotometric instrument, the samples are held in square cuvettes with ground and polished plane sides so that the sample container contributes little or no uncertainty to the measurement. In the field it is desirable to use inexpensive and disposable cylindrical plastic test tubes. However, these test tubes may contribute significantly to the uncertainty of the measurement. A typical plastic tube suffers three principal defects:

(a) it may be scratched to a greater or lesser degree, depending on the care with which it is handled; these scratches tend to scatter and diffuse light, making the light path indeterminate;

(b) it may contain striations or irregularities in the wall of the tube, which will refract light in an indeterminate way; and (c) the tube's exterior and interior may not be concentric, so that the actual path length and direction of a light ray passing through the sample depends on the orientation of the tube.

The degree to which these imperfections contribute uncertainty is highly dependent on the details of the optical design.

Figure 4:
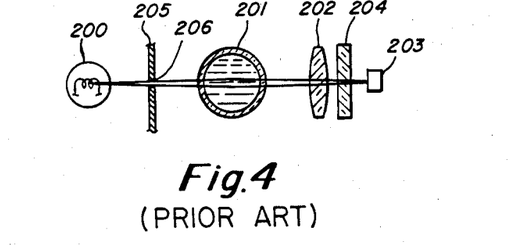
FIG. 4 is an illustrative top view of a prior art optical system.

In the prior art design shown in FIG. 4, a narrowly collimated or focused beam of light from a lamp 200 passes through a sample tube 201 and then through a lens 202 which focuses the beam on a photodetector 203 which is sensitive to a predetermined wavelength. A screen 205 having an aperture 206 is disposed between the lamp and tube to prevent stray light from reaching the photodetector. A filter 204 is disposed between the lens and photodetector for selecting light of a predetermined wavelength. In this prior art design, it is desirable to pass a very narrow beam of light through the center of the tube only so that the light beam passes through a sample area having a roughly uniform thickness. This is required where a quantitative determination of absorbance is being made and it is necessary to know the dimensions of the sample through which the beam passes. However, individual defects in the area of the sample tube through which the beam passes have a significant effect on the photodetector output.

All of the above-mentioned defects in the plastic sample tubes affect the measurement results of this prior art design very severely. Typically, a measurement in absorbance may contain an error of 0.05 to 0.1 as a result of tube defects alone. The amount of error is highly dependent on the individual tube under test and its orientation.

Two designs have been found to be highly effective at minimizing the errors caused by sample tube defects. These designs are shown in FIGS. 2 and 3.

Figure 2:
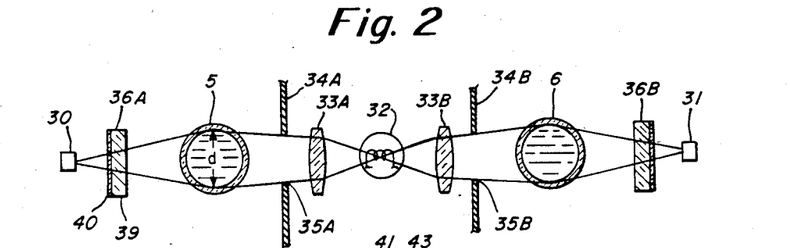
FIG. 2 is an illustrative top view of a first embodiment of the optical subsystem of this invention.
Figures 2A, 3:
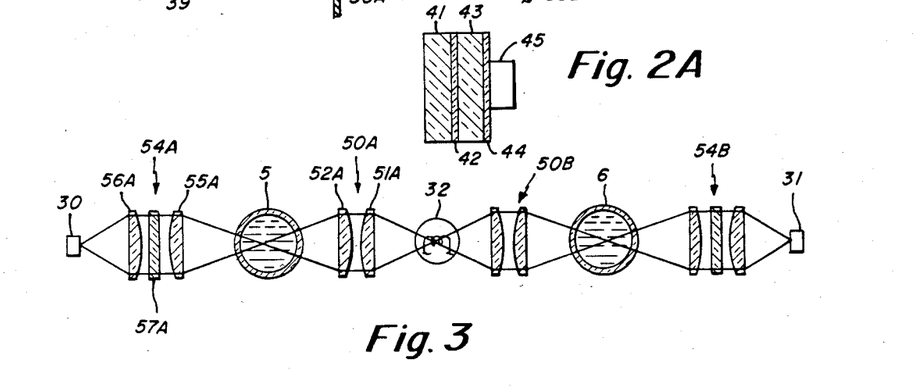
FIG. 2A is an illustrative top view of the filter/diffuser and photodetector combination of this invention.
FIG. 3 is an illustrative top view of a second embodiment of the optical subsystem of this invention.

A first embodiment of the optical subsystem is shown in FIG. 2. A pair of photodetectors 30, 31 are positioned at opposite ends of an axial line. A light source means 32, such an incandescent lamp, is centered at the midpoint of the axial line. A first sample tube 5 and a second sample tube 6 are identically positioned on the axial line on opposite sides of the lamp, between the lamp and an associated photodetector. A collimating lens 33A(33B) and a screen 34A(34B) having an aperture 35A(35B) are identically positioned on either side of the lamp between the associated sample tube 5(6) and lamp 32. A filter/diffuser 36A(36B) is positioned between the associated sample tube 5(6) and associated photodetector 30(31).

The object of this first design is to spread the illumination over substantially the entire width of the sample tube so that the net light transmitted to the photodetector is averaged over many scratches and defects and is minimally dependent on the lack of concentricity of the inner diameter and outer diameter of the tube. While the operation of the optical system with respect to sample tube 5 is described herein, the operation with respect to sample tube 6 is identical.

The collimating lens 33A is positioned between the sample tube 5 and light source 32 and spaced slightly closer to the light source than the focal point of the lens so that the lens transmits a slightly divergent beam to the sample tube. The screen 34A prevents stray light beams from reaching the photodetector 30. Further, the height of the aperture 35A is restricted to prevent light from hitting the meniscus of the liquid sample in the tube or the bottom of the tube and reflecting into the photodetector. The sample tube 5 is spaced with respect to the lens 33A such that the outer diameter of the divergent beam at the center plane of the tube is equal to or slightly less than the inner diameter d of the tube. The sample tube acts as a cylinder lens to focus the beam at a vertical focal line and the photodetector is spaced slightly ahead of the focal line so that the beam strikes a large area of the photodetector. This insures a photodetector signal of large amplitude and averaged value.

The combination filter/diffuser 36A disposed between the sample tube 5 and photodetector 30 consists of a filter glass 39 for selecting a predetermined wavelength of light and a diffusive sheet or film 40 covering the surface of the filter glass adjacent the photodetector. For example, film 40 may be Mylar TM film frosted on both sides and about 0.006" (0.15 mm) thick. Because scratches and defects in the sample tube cause light to bounce in a random manner, the diffusive sheet 40 is provided to produce an averaging effect so that the photodetector output is less dependent on defects in the sample tube. Preferably, the photodetector 30 is sensitive to the same predetermined wavelength as the filter glass 39.

A preferred embodiment of the filter/diffuser is shown in FIG. 2A. Two pieces of filter glass 41, 43 and two sheets of diffusive film 42, 44 are sandwiched together and disposed adjoining a photodetector 45. Diffusive sheet 42 is sandwiched between filter glasses 41 and 43, and diffusive sheet 44 is sandwiched between filter glass 43 and photodetector 45. This filter/diffuser is preferred because the addition of a second diffusive film separated from the first aids in a more uniform diffusion of the light. The use of a second filter glass is necessary in most cases in order to limit the bandwidth of the light transmitted. Further, adjoining the photodetector 45 to diffusive layer 44 eliminates light loss and increases the amplitude of the photodetector output.

A second embodiment of the optical subsystem of this invention is shown in FIG. 3. Again, the design spreads the light beam over a large area of possible defects in the tube. A first lens set 50A includes a pair of diametrically opposed lenses 51A, 52A positioned on an axial line between the sample tube 5 and light source 32. Collimating lens 51A is disposed adjacent the light source and has a focal point at the light source. Converging lens 52A is disposed adjacent the sample tube and has a focal point at the center of the sample tube. A second lens set 54A includes a second pair of diametrically opposed lenses 55A, 56A positioned on the axial line between the sample tube 5 and photodetector 30. Collimating lens 55A is disposed adjacent the sample tube and has a focal point at the center of the sample tube and converging lens 56A is disposed adjacent the photodetector and has a focal point at the photodetector.

In the second embodiment, because the light rays pass perpendicularly through the sample tube and the tube has no focusing effect, irregularities of the tube do not affect the focal point. Thus, the space between the lenses and sample tube is less critical in this design. Furthermore, in the second embodiment a filter 57A can be placed between the two lenses 55A, 56A of the second lens so that the light rays pass through the filter as parallel rays. This minimizes refractions at the surface of the filter and thus reduces light loss.

In FIG. 3, the first and second lens sets 50B and 54B between the lamp 32, sample tube 6 and photodetector 31, are identical to those of 50A and 54A previously described.

To evaluate the effectiveness of the designs shown in FIGS. 2 and 3, in comparison with the prior art design of FIG. 4, a series of measurements was taken with one particular sample tube filled with a sample solution. Eight different orientations of the tube were tried for each design to find the range of readings resulting from the one sample and tube. The resulting inaccuracy can be expressed as an error in absorbance as follows:

$$\Delta A = \log[(I_{max} - I_{min})/2I_{av}]$$

where $I_{max}$ = maximum light intensity resulting from the series of readings for a given sample, tube and optical design;

$I_{min}$ = minimum light intensity resulting from the series of readings for a given sample, tube and optical design; and $I_{av}$ = average light intensity resulting from the series of readings for a given sample, tube and optical design.

Design 1 was that shown in FIG. 2 with lens 33A having a diameter of 5/16" and a focal length of ⅜". Lens 33A was spaced 0.27" from lamp 32, screen 34A, having an aperture 0.125"×0.275", was spaced 0.40" from lens 33A, tube 5 was spaced 0.35" from screen 34A, and photodiode 30 was spaced 0.65" from tube 5 (all distances are from center point of element). The filter/diffuser used was that shown in FIG. 2A wherein 41 was a 2 mm thick filter glass, model GG-435 by Schott, imported by ESCO Products, Inc. of Oak Ridge, N.J., and 43 was a 4.0 mm thick filter glass, model 5-58 by Corning Glass Works of Corning, N.Y. Each filter glass had a diameter of 5/16". The diffuser sheets 42 and 44 were Mylar ™ film, each 0.006" thick and frosted on both sides. The photodiode was adjoining sheet 44.

Design 2 was that shown in FIG. 3 with lenses 51A, 52A, 55A and 56A each having a diameter of ⅜" and a focal length of ½". The first lens set was spaced 0.5" from lamp 32, tube 5 was spaced 0.5" from the first lens set, lens 55A was spaced 0.5" from tube 5, lens 56A was spaced 0.25" from lens 55A, and photodiode 30 was spaced, 0.5" from lens 56A (all distances are from center point of element). Two filter glasses, the same as 41 and 43 described in design 1 (but without diffusive sheets 42 and 44) were used. In design 2, the distance between the lenses and sample tube could be changed up to 1/16" (1.6 mm) without changing the photodetector reading significantly. In comparison, in design 1, the sample tube had to be spaced within 5/1000" (0.13 mm) with respect to the lens and with respect to the axial line extending between the lamp and photodetector to insure a consistent photodetector reading.

The prior art design was that shown in FIG. 4 with lens 202 having a diameter of 5/16" and a focal length of ⅜". Screen 205 had an aperture 206 of 1/10" in height. The same two filter glasses described for design 2 were used.

In all designs an incandescent lamp was used, model 158X sold by Gilway of Woburn, Mass. The sample tube was made of polystrene having a length of 75 mm, an outer diameter of 75 mm, and an inner diameter of 9 mm. The photodiode was model S-1133 sold by Hamamatsu of San Jose, Calif.

The following values of $\Delta A$ were obtained for the prior art design and designs 1 and 2 of the present invention:

| PRIOR ART DESIGN | $\Delta A = .05$ |
|---|---|
| DESIGN 1 | $\Delta A = .01$ |
| DESIGN 2 | $\Delta A = .004$ |

Thus, it has been shown that both design 1 and design 2 of this invention give substantially better results than the prior art design. While it would appear that design 2 is preferable over design 1, other factors such as cost, size, complexity and the required accuracy of construction mitigate in favor of design 1.

Figure 6A:
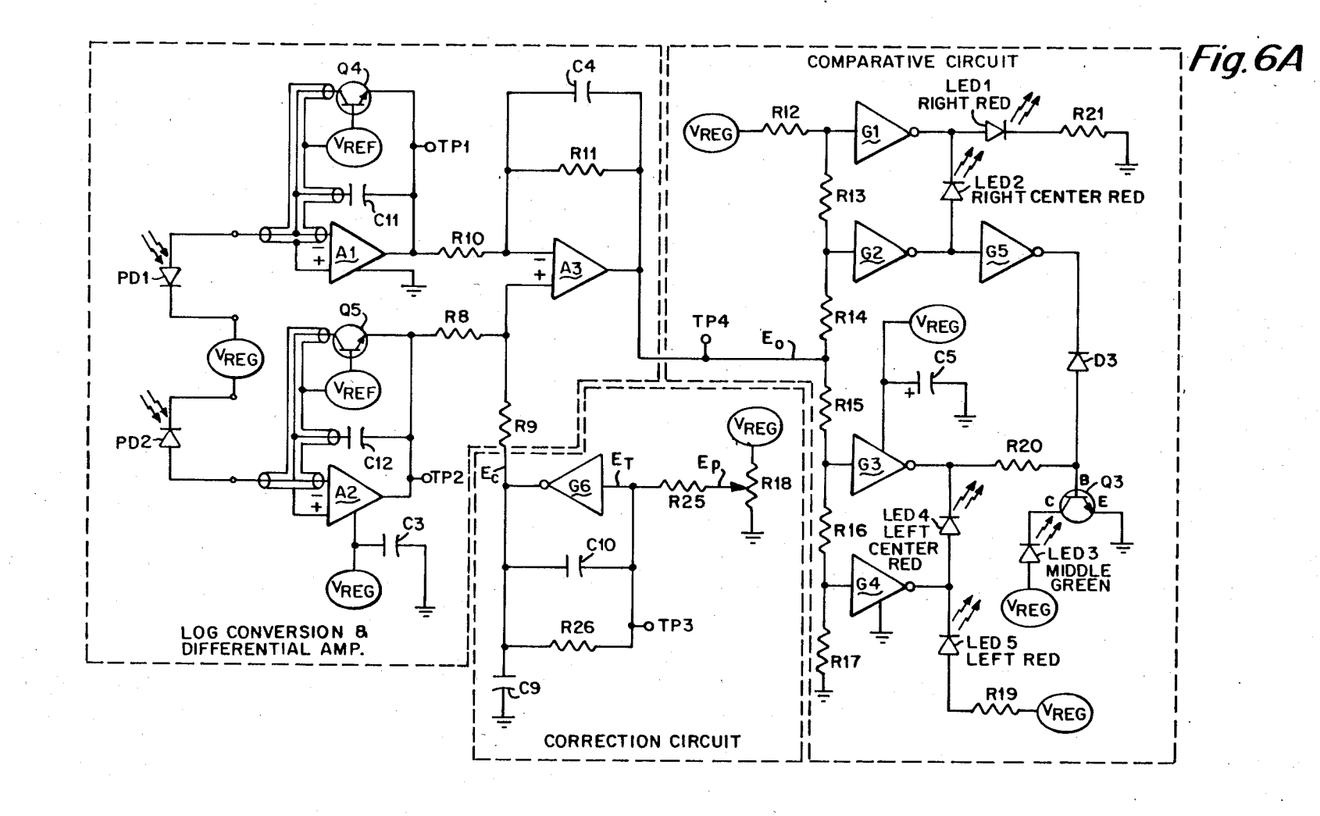
FIG. 6A is a schematic diagram of three major portions of the electronic subsystem of this invention, including the log conversion and differential amplifier circuit, the correction circuit, and the comparative circuit.

The electronic subsystem of the present invention, as shown in FIG. 6A, performs the following functions:

(a) the current outputs $ID_1$ and $ID_2$ of the two photodiodes PD1 and PD2 are logarithmically converted to voltage signals;

(b) the two voltage signals are differentially amplified at A3 to produce a difference signal $E_0$;

(c) the difference signal $E_0$ is compared to a plurality of predetermined reference voltages with a series of voltage comparators, consisting of digital gate means $G_1$-$G_5$ and resistive chain R12-R17;

(d) the digital gate means drive a plurality of indicator LEDs 1-5 (corresponding to indicator lights 15-19 in FIG. 1) to indicate the relative value of the difference signal with respect to the reference voltages; and (e) a correction circuit is provided so that the difference signal $E_0$ is referenced to the threshold voltage $E_T$ of the digital gate means.

The indicator lights or LEDs 15-19 of FIG. 1, which correspond to LED's 1-5 of FIG. 6A respectively, indicate the degree of difference in optical density between the samples in the tubes. If the sample and standard solutions have equal optical densities, then a middle green LED 17 turns on to indicate the same. If the solution of tube 5 has a lesser optical density than the solution of tube 6, when the difference exceeds a first predetermined level the comparator will trigger a right center red LED 18 and simultaneously extinguish the green LED, and if the difference exceeds a larger second predetermined level, then a right red LED 19 will light. At no time is more than one indicator LED on. If the solution of tube 5 has a greater optical density than the solution of tube 6, then the left center red LED 16 and left red LED 15 will light in the same manner as described for those to the right of center. A typical configuration is for the right center LED 18 (and left center LED 16) to come on at $\Delta A = 0.03$ O.D. (difference in absorbance between the tubes is 0.03), and the right LED 19 (and left LED 15) to comes on at $\Delta A = 0.1$ O.D.

Figure 6B:
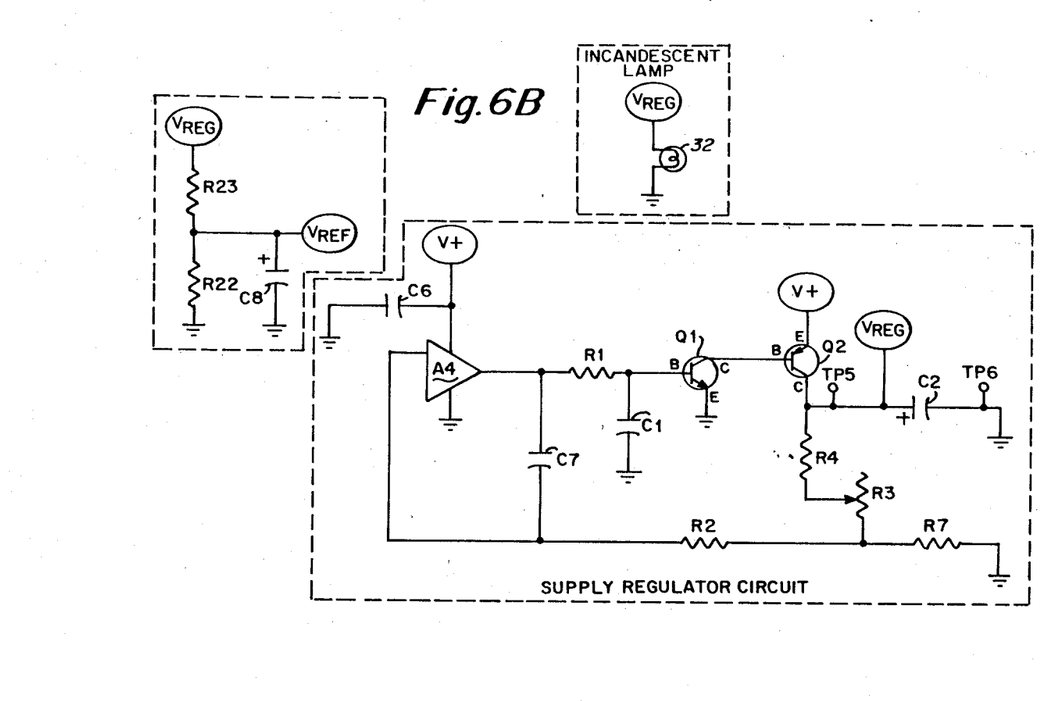
FIG. 6B is a schematic diagram of the supply regulator circuit and an incandescent light source.

The operating voltage $V_{REG}$ for the lamp and the electronic subsystem is stabilized at 2.000 volts by the supply regulator circuit shown in FIG. 6B. The circuit includes amplifier A4, capacitors C1, C2, C7, C8, resistors R1, R2, R3 (variable), R4, R7, R22, R23, transistors Q1, Q2, battery V+, and internal regulator $V_{REF}$. A range of battery voltages V+ from 3.0 to 2.1 volts can be accommodated without degrading performance. Lamp life is extended substantially by operating the lamp 32 at a constant 2.0 volts.

The regulator circuit is built around one section of a amplifier A4 specifically intended for voltage regulation. A4 in this preferred embodiment is amplifier U4 LM10CLN sold by National Semiconductor of Santa Clara, Calif. The LM10CLN drives transistors Q1 and Q2 as required to regulate $V_{REG}$ to exactly 2.000 volts. An internal regulator provides a constant $V_{REF}$ of 0.2 volts. $V_{REG}$ is divided down to 0.2 volts and then compared to this reference. $V_{REF}$ is also used to determine the operating points of the operational amplifiers A1 and A2 as shown in FIG. 6A.

To compute the difference signal $E_0$, the two diode currents $I_{D1}$ and $I_{D2}$ are logarithmically converted to voltage signals and the two voltage signals are differentially amplified. The stability of the logarithmic conversion and differental amplification is such that an overall electronic error budget of 0.005 O.D. is not violated over the life of the instrument.

Figure 5:
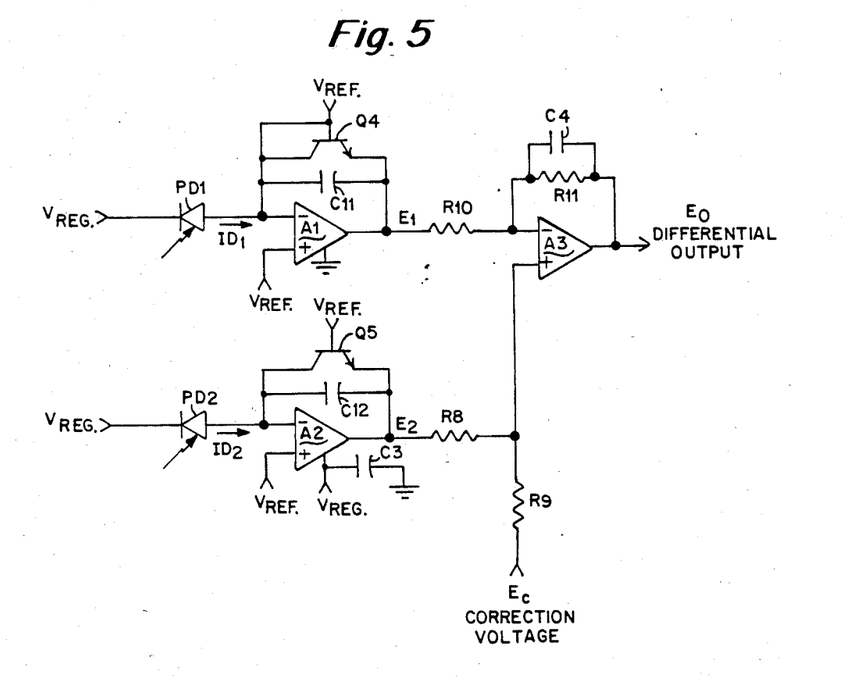
FIG. 5 is a schematic diagram showing the circuit means for logarithmically converting the current outputs of the photodiodes to voltage signals and means for differentially amplifying the resultant voltage signals to produce a difference signal.

FIG. 5 shows the log conversion and differential amplifier circuit for generating the difference signal $E_0$. Light from light source 32 which passes through sample tube 5 and strikes photodiode PD1 generates a current $I_{D1}$. Likewise, light from light source 32 which passes through sample tube 6 and strikes photodiode PD2 generates a current $I_{D2}$. The photodiode currents can be expressed as:

$$I_{D1} = k_1 g_1 f_1 I \qquad (1)$$

$$I_{D2} = k_2 g_2 f_2 I \qquad (2)$$

where I is the total intensity of light source 32, $f_1$ and $f_2$ are the fractions of light absorbed by the samples in tubes 5 and 6 respectively, $g_1$ and $g_2$ are the fractions of light passing through tubes 5 and 6 which actually reach the photodiodes PD1 and PD2 respectively, and $k_1$ and $k_2$ are the efficiencies with which the photodiodes PD1 and PD2 convert the light reaching their surfaces respectively.

The diode currents $I_{D1}$ and $I_{D2}$ constitute optical density signals representative of the optical densities of the samples in tubes 5 and 6 respectively. The diode currents $I_{D1}$ and $I_{D2}$ are logarithmically converted to voltage signals $E_1$ and $E_2$ by a pair of identical log conversion circuits shown in FIGS. 5 and 6A. Thus, amplifier A1, capacitor C11, and transistor Q4, arranged in parallel, convert $I_{D1}$ to $E_1$, and similarly, amplifier A2, capacitor C12, and transistor Q5, arranged in parallel, convert $I_{D2}$ to $E_2$. A1 and A2 are from the same package and are identically powered by connection to the regulated supply voltage $V_{REG}$ and decoupling capacitor C3 (as shown for A2) and grounded (as shown for A1). Because the log conversion circuits are identical, the votages $E_1$ and $E_2$ may be expressed as:

$$E_1 = K \log I_{D1} \qquad (3)$$

$$E_2 = K \log I_{D2} \qquad (4)$$

where K is a constant.

The voltage signals $E_1$ and $E_2$ are differentially amplified at A3 to produce a difference signal $E_0$ as set forth below:

$$E_0 = G(E_2 - E_1) + E_c \qquad (5)$$

where G is the amplifier gain and $E_c$ a correction voltage. The correction voltage $E_c$ is added to the positive input of A3 for reasons discussed hereinafter. The differential amplifier circuit includes differential amplifier A3, capacitor C4, and resistors R8, R9, R10, and R11, where $R8 = R10 = R_A$ and $R9 = R11 = R_B$. The amplifier gain $G = R_B/R_A$ is maintained constant through careful selection of the gain resistors. Selecting the value of the gain is also described hereinafter.

By substituting equations 1–4 into equation 5, the following equation for $E_0$ is obtained:

$$E_0 = KG\log[(k_2 g_2)/(k_1 g_1)] + KG\log(f_2/f_1) + E_c \qquad (6)$$

The ratio of photodiode efficiencies $k_2/k_1$ is constant over time given equal wavelength of the incident light, equal temperature and equal reverse bias. Dark current will drift somewhat but is not a limitation in this application.

The ratio $g_2/g_1$ of optic path efficiencies depends on the details of the design and its implementation. If we assume perfect sample tubes and an unchanging rigid geometry, then the ratio $g_2/g_1$ is fixed.

Since the amplifier gain G is maintained constant through careful selection of gain resistors, and K is a constant, the entire first term in (6) is a constant C. Thus, the difference signal $E_0$ can be represented as follows:

$$E_0 = C + KG\log(f_2/f_1) + E_c \qquad (7)$$

C can be compensated for by a simple additive offset applied at the input of the differential amplifier A3. This is accomplished by the correction circuit discussed hereinafter. The connection circuit further references the difference signal $E_0$ to the threshold voltage $E_T$ of the hex inverters used in the comparative circuit so that $E_0 = E_T$ when the optical densities of the two samples are equal.

The difference signal $E_0$ generated by $A_3$ is sent to the comparative circuit shown in FIG. 6A, wherein $E_0$ is compared to a series of predetermined reference voltages to determine to the relative value of the difference signal with respect to the reference voltages. The act of comparison is performed by a plurality of low cost digital integrated circuits. In the preferred embodiment, hex inverters such as the 74HC04 sold by Motorola of Austin, Tex. are used as the digital IC gates means. The hex inverters are used in the configuration shown in FIG. 6A in order to economize on parts count and cost.

The output from the differential amplifier $E_0$ is divided by a resistive chain so that the voltage at each node of the chain is directly related to $E_0$. The resistive chain consists of resistors R12, R13, R14, R15, R16 and R17 arranged in series between $V_{REG}$ and ground. Connected to each node is an input of one of hex inverter gates G1, G2, G3, and G4. Gates G1–G5 are all in the same package and each is connected to the regulated supply voltage $V_{REG}$ and to decoupling capacitor C5 (as shown for G3) and to ground (as shown for G4). If the node happens to be above the switching threshold of the gate, which for the 74HC04 is about ½ of the regulated supply voltage $V_{REG}$, then the gate output is low. Conversely, if the node is below the threshold, then the gate output is high. All of the gates are selected from a single package so they have very nearly the same threshold for a given temperature and supply voltage.

The outputs of gates G1–G4 are connected to drive indicator LEDs 1–5. Thus, in addition to the resistive chain and hex inverter gages G1–G4, the comparative circuit further includes indicator LEDs 1–5, resistors R19, R20 and R21, diode D3, transistor Q3, and hex inverter gate G5 as shown in FIG. 6A. The indicator LEDs are arranged such that only one LED is on at a time. The operation of the comparative circuit is thus understood by determining its operation under three circumstances, when the optical densities of the two samples are equal, when the optical density of the first sample is greater than the second, and when the optical density of the second sample is greater than the first.

Thus, when $I_{D1} = I_{D2}$, i.e., the optical densities of the two samples are equal, then the voltage at TP4 ($E_0$) will be $E_T$. The gate outputs of G2 and G1 will be low so that the right center red LED 2 and right red LED 1 will be off. The gate outputs of G3 and G4 will be high so that the left center red LED 4 and left red LED 5 will also be off. However, because the gate output of G5 and G3 will both be high, transistor Q3 will conduct and the green middle LED 3 will be on indicating that the two solutions have equal optical densities.

By way of further example, if $I_{D1}$ is greater than $I_{D2}$ by up to a first predetermined value, e.g., 0.03 O.D., then the outputs of G2, G3 and G4 will be high and the output of G1 will be low. All LED's will be off except for the right center red LED 2 which will be on to indicate that the absorbence of the sample in tube 6 is greater than the absorbence of the sample in tube 5, but by no more than 0.03 O.D. If the absorbence of the sample in tube 6 is greater than that of the sample in tube 5 by at least a second predetermined value, e.g., 0.1 O.D., then the left red LED 1 will be on, and all other LED's off.

Similarly, if $I_{D1}$ is less than $I_{D2}$ by up to 0.03 O.D., then the outputs of G1, G2 and G3 will be low and G4 will be high. Thus the left center red LED 4 will be on to indicate that the absorbence of the sample in tube 5 is greater than the absorbence of the sample in tube 6 by no more than 0.03 O.D. Further, if the absorbence of the sample in tube 5 is greater than that of the sample in tube 6 by at least 0.1 O.D., then the left red LED 5 will be on and all other LED's off.

The correction circuit provides both a zeroing mechanism to account for the fact that the two light paths and photodetectors are not truly identical and further provides a compensation factor to account for variations in the threshold voltage $E_T$ of the hex inverters used in the comparative circuit. The output of the correction circuit shown in FIG. 6A is a correction voltage $E_c$ which is applied to the positive input of A3.

The correction circuit includes a hex inverter G6 from the same package as the hex inverters G1-G5 used in the comparative circuit. A trim potentiometer R18, having an output voltage $E_p$, is provided along with resistors R25 and R26 and capacitors C9 and C10.

Figure 7:
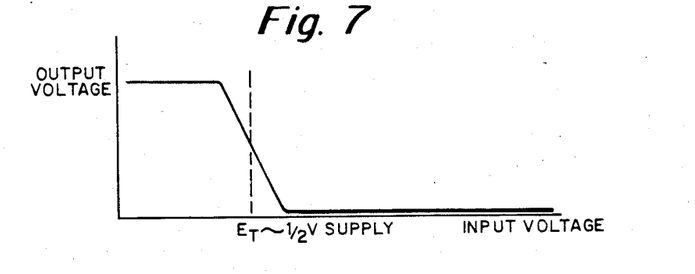
FIG. 7 is an illustration of the transfer characteristic for an IC digital hex inverter.

The switching threshold of the hex inverter G6 is about one-half of the regulated supply voltage $V_{REG}$. This logic gate is quite abrupt in its action and all of the gates in the package have very nearly the same threshold voltage $E_T$ for a given temperature and supply voltage. The transfer characteristic of the hex inverter is shown in FIG. 7. The slope of the transfer characteristic in the region of $E_T$ is the gain of the hex inverter if it is considered as an amplifier. With the gate output tied to the input, the input and output will stabilize at a value which is called the threshold or switching point $E_T$. The absolute value of $E_T$ varies from one batch of devices to another, and varies according to time, temperature, and supply voltage. All of the inverters in a package have the same threshold within a few milivolts. By utilizing G6 in the correction circuit as an amplifier as shown in FIG. 6A, the difference signal $E_0$ is referenced to the threshold voltage of G6.

Another function of the correction circuit is to compensate for differences between the optical paths during the initial set-up procedure. For this purpose, the trim-potentiometer R18 is introduced to the circuit. The circuit will stabilize with the input voltage at $E_T$ if the trim-pot is adjusted to a value $E_p$, where $$(E_p - E_c)R_d = (E_p - E_T)(R_c + R_d) \quad (8)$$

where $R26 = R_c$ and $R25 = R_d$.

During initial calibration of the device, $f_2$ is made equal to $f_1$ (equal samples) so that $KG\log(f_2/f_1) = 0$. The trim-pot is adjusted until the voltage $E_0 = E_T$. Now, if $E_T$ changes following calibration, $E_0$ will follow the change in $E_T$ as set forth below:

$$E_0 = E_T + KG\log(f_2/f_1) \quad (9)$$

Thus, if the value of $E_T$ drifts upward, the output $E_0$ will also. At the same time, the voltage inputs for each of the comparator circuits will be going up by the same amount. The output of the differential amplifier is thus fully and exactly compensated for drift in $E_T$. At the same time the initial differences in the optical paths are corrected with one trim-pot adjustment.

Figure 6C:
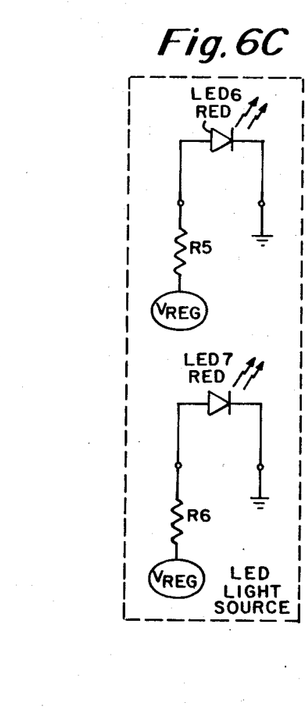
FIG. 6C is a schematic diagram of an alternative light source comprising two LED's.

While the incandescent lamp 32 shown in FIG. 6B is the preferred light source, alternatively, a pair of diametrically opposed LED's can be used as light sources, one to illuminate each of sample tubes 5 and 6. FIG. 6C shows a circuit for driving red LED 6 and red LED 7.

While the invention is not so limited, the following table of values for the circuit elements shown in FIGS. 5, 6A, 6B and 6C are an example of an operative circuit according to this invention.

TABLE 1

| | |
|---|---|
| A1 | U1 25L2 CP |
| A2 | U1 25L2 CP |
| A3 | U4 LM10C LN |
| A4 | U4 LM10C LN |
| C1 | .01 uF |
| C2 | 10 uF |
| C3 | .01 uF |
| C4 | .22 uF |
| C5 | 1 uF |
| C6 | .01 uF |
| C7 | .1 uF |
| C8 | 1 uF |
| C9 | .01 uF |
| C10 | .01 uF |
| C11 | 100 pF |
| C12 | 100 pF |
| D3 | CR1 1N6263 |
| G1 | U3 74HC04 |
| G2 | U3 74HC04 |
| G3 | U3 74HC04 |
| G4 | U3 74HC04 |
| G5 | U3 74HC04 |
| G6 | U3 74HC04 |
| Q1 | PN2222 |
| Q2 | TIP32C |
| Q3 | PN2222 |
| Q4 | U2 LM394N |
| Q5 | U2 LM394N |
| R1 | 470Ω |
| R2 | 10KΩ |
| R3 | 2KΩ, 20 turn |
| R4 | 9.1KΩ** |
| R5 | 100Ω |
| R6 | 100Ω |
| R7 | 1KΩ** |
| R8 | 7.68KΩ* |
| R9 | 499KΩ* |

TABLE 1-continued

| | |
|---|---|
| R10 | 7.68KΩ* |
| R11 | 499KΩ* |
| R12 | 9.1KΩ** |
| R13 | 1.0KΩ** |
| R14 | 1.0KΩ** |
| R15 | 1.0KΩ** |
| R16 | 1.0KΩ** |
| R17 | 9.1KΩ** |
| R18 | 10KΩ, 20 turn |
| R19 | 100Ω |
| R20 | 10KΩ |
| R21 | 100Ω |
| R22 | 3.9KΩ |
| R23 | 10KΩ |
| R24 | — |
| R25 | 100KΩ** |
| R26 | 56KΩ** |

*ultra-stable 1% resistors, matched to .1%, 25 PPM
**1% metal film resistors

The operational amplifier U1 25L2 CP is sold by Texas Instruments of Dallas, Tex. The differential amplifier U4 LM10CLN is sold by National Semiconductor of Santa Clara, Calif. The diode CR1 1N6263 is sold by Hewlett-Packard of Palo Alto, Calif. The hex inverter U3 74HC04 is sold by Motorola of Austin, Tex. The transistors PN2222, TIP32C, and U2 LM394N, are all sold by National Semiconductor of Santa Clara, Calif.

In designing the electronic subsystem of this invention, it is necessary to set the gain of differential amplifier A3 by selecting appropriate values for the gain resistors R8, R9, R10, and R11. The selection is made so that the indicator LEDs 1–5 come on for predetermined differences in absorbance which are of importance for the test at hand. One method for setting the gain of A3 is to use known sample solutions which have been accurately measured in a laboratory spectrophotometric instrument. Alternatively, the required gain can be calculated. To do so, one must understand the difference between the concepts of absorbance and absorptivity. An example of the calculations required to set the gain of A3 is described hereinafter.

The definition of absorbance is:

$$A = \log I/I_o$$

where $I_o$ is the intensity of light transmitted when the sample tube is filled with completely clear fluid and I is the light transmitted when the actual sample is in place. See Skoog and West, "Principles of Instrumental Analysis," Saunders College, Philadelphia, Pa., 1980.

If one compares two samples which transmit amounts of light $I_1$ and $I_2$, then the differential absorbance $\Delta A$ is of interest where:

$$\Delta A = \log I_2/I_o - \log I_1/I_o = \log I_2/I_1 \quad (10)$$

Beer's law relates light absorbance to the properties of the sample under test:

$$A = abc$$

where a=absorptivity of the solution, b=path length, and c=concentration of the solution.

Specific absorptivity is defined as:

$$\alpha = ac \quad (11)$$

This is the measure of absorbance per unit path length, and is dependent on the sample's nature and concentration. Thus:

$$A = \alpha b$$

If one compares two different solutions in identical sample containers, then the differential absorbance is:

$$\Delta A = A_2 - A_1 = b(\alpha_2 - \alpha_1) = b\Delta\alpha \quad (12)$$

When a sensitivity of 0.03 units of absorbance is desired, what is really required is a specific differential absorptivity $\Delta\alpha = 0.03$ since this is the quantity which is independent of the means of measurement. Combining equations (10) and (12) produces:

$$\Delta\alpha = (1/b)\Delta A = (1/b)\log(I_2/I_1)$$

It is convenient to use natural logarithms (ln), so that $$\Delta\alpha = (1/2.3026b)\ln(I_2/I_1) \quad (13)$$

Further one must consider the path length b for a particular instrument. Thus, for the optical configuration of FIG. 2, one may consider as an approximation that the light rays pass directly through the sample tube without refraction. Then, it can be shown geometrically that the average path length through the solution is $$b_{av} = (\pi/4)d$$

where d is the inner diameter of the sample tube. This is the value of path length which must be used in a calculation for specific differential absorptivity:

$$\Delta\alpha = [4/(2.3026\pi d)]\ln(I_2/I_1) \quad (14)$$

Equation (14) relates specific differential absorptivity to light intensities. In addition one needs to determine the relationship between light intensities and $E_0$, the output of the differential amplifier.

The characteristic of the LM394 log conversion circuit is that of an ideal silicon diode, for which $$V_f = (T/11,600)\ln(I_f/I_s)$$

where $V_f$=forward voltage, T=absolute temperature °K, $I_f$=forward current and $I_s$=saturation current for that diode.

The two LM394s which are used in the two log amplifiers are housed in the same package and come very well matched from the factory, so that $I_s$ is the same for both. The forward current $I_f$ is just equal to the photodiode current caused by the incident light:

$$I_{f1} = I_{D1}$$

$$I_{f2} = I_{D2}$$

The differential amplifier extracts the difference in voltage between the two log conversion circuits and amplifies it by a factor G (gain):

$$E_0 = G(V_{f2} - V_{f1})$$

which reduces to:

$$E_0 = (GT/11,600)\ln(I_{D2}/I_{D1})$$

Diode current $I_D$ is proportional to light intensity I at the diode:

$$I_{D2} \alpha I_2$$

$$I_{D1} \alpha I_1$$

so
$$E_0 = (GT/11,600)\ln(I_2/I_1)$$

Combining this result with equation (5):

$$\Delta\alpha = [4/(2.3026\pi d)][(11,600\, E_0)/GT]$$

or $$E_0 = (2.3026\pi d G T \Delta)/[(4)(11,600)] \quad (15)$$

For this example, we want to have $\Delta\alpha = 0.03$ when the first red light (i.e., LED2 or LED4) comes on. The first red light comes on when $E_0 = 0.100$ volts, as is determined by the resistor chain to which the hex inverter inputs are attached.
Given
 $\Delta\alpha = 0.03$
 $T = 298°$ K (room temperature)
 $d = 9$ mm $= 0.9$ cm
 $E_0 = 0.100$ volts
Then equation (15) can be solved to give $G = 79.7$ as the required gain. Thus we need to choose $$R11/R10 = R9/R8 = 79.7$$

This calculation provides results as close as those which have been determined by experimental means.

Although a preferred embodiment of the invention has hereinbefore been described, it will be appreciated that variations of this invention will be perceived by those skilled in the art, which variations are nevertheless within the scope of this invention as defined by the claims appended hereto.

What is claimed is:

1. An improved optical system for a colorimeter of the type wherein the optical density of a liquid in a cylindrical optically transparent sample tube is determined by passing a beam of light from a light source through the liquid and onto a photodetector, said optical system comprising:
   a collimating lens positioned between the sample tube and light source and spaced closer to the light source than the lens transmits a divergent beam to said sample tube;
   said sample tube being spaced with respect to the lens so that the outer diameter of said divergent beam at the center plane of said tube is substantially equal to the inner diameter of said tube; and
   said sample tube acting as a cylinder lens to focus said beam at a vertical focal line and said photodetector being spaced slightly ahead of said focal line so that the beam strikes a substantial portion of said photodetector.

2. The optical system of claim 1, further including a combination filter/diffuser positioned between the sample tube and photodetector, said combination filter/diffuser comprising a filter for selecting a predetermined wavelength of light and a light-diffusing layer for averaging the effect of individual defects in the sample tube so that the photodetector output is substantially unaffected by said defects.

3. The optical system of claim 2, wherein said light-diffusing layer is disposed over the surface of said filter adjacent the photodetector.

4. The optical system of claim 2, wherein a plurality of said combination filter/diffusers are connected in serial arrangement and said photodetector adjoins a light-diffusing layer at one end of the series.

5. The optical system of claim 2, wherein said light-diffusing layer is Mylar TM film which is frosted on both sides.

6. The optical system of claim 1, wherein the lens is spaced at least about 28% closer to the light source than the focal point of the lens.

7. The optical system of claim 6, wherein the lens is spaced about 28% closer to the light source than the focal point of the lens.

8. Apparatus for determining the optical density of a liquid sample, said apparatus comprising:
   (a) a light source which emits an illuminating beam;
   (b) a photodetector which detects a measuring beam;
   (c) a cylindrical, optically-transparent sample tube which is closed at one end for holding a liquid sample, the optical density of which is to be measured;
   (d) a collimating lens positioned between the sample tube and the light source to receive the illuminating beam and being spaced closer to the light source than the focal point of the lens so as to transit a divergent beam to the sample tube, said beam having an outer diameter at the centerline of the tube which is substantially equal to the inner diameter of the tube; and
   (e) a light-diffusing means positioned between the sample tube and photodetector;
   wherein the divergent beam is spread over substantially the entire width of the sample tube so that the measuring beam transmitted to the photodetector is averaged over any of the scratches or defects in the sample tube and is minimally dependent upon any lack of concentricity of the inner and outer diameters of the tube;
   wherein the sample tube acts as a cylindrical lens which transmits the measuring beam to the photodetector, the photodetector being spaced slightly ahead of the focal line of the tube lens so that the measuring beam strikes a substantial portion of the photodetector to produce a photodetector output of large amplitude and averaged value;
   and wherein the light-diffusing means produces an averaging effect on the measuring beam to further reduce the dependence of the photodetector output on defects in the sample tube.

* * * * *

UNITED STATES PATENT AND TRADEMARK OFFICE
CERTIFICATE OF CORRECTION

PATENT NO. : 4,797,000
DATED : January 10, 1989
INVENTOR(S) : Curtis

It is certified that error appears in the above-identified patent and that said Letters Patent is hereby corrected as shown below:

Col. 15, line 48 -  after "the" insert -- focal point of the --.

Col. 15, line 48 -  after "lens" insert -- so that the lens --.

Col. 15, line 16 -  equation should read --

$$E_0 = (2.3026 \, \eta \, dGT \Delta \lambda)/[(4)(11,600)] \quad (15)$$ --

Col. 12, line 12 -  equation should read --

$$(E_p - E_c)R_d = (E_p - E_T)(R_c + R_d) \quad (8)$$ --

Col. 7, line 68 - change "75" to -- 12 --.

Signed and Sealed this

Fourteenth Day of November, 1989

Attest:

JEFFREY M. SAMUELS

Attesting Officer    Acting Commissioner of Patents and Trademarks